US00PP24326P3

(12) United States Plant Patent
Kristensen

(10) Patent No.: US PP24,326 P3
(45) Date of Patent: Mar. 18, 2014

(54) ***OSTEOSPERMUM* PLANT NAMED 'SAKOST8194'**

(50) Latin Name: *Osteospermum hybrida*
Varietal Denomination: SAKOST8194

(75) Inventor: Niels G. Kristensen, Grauballe (DK)

(73) Assignee: Sakata Ornamentals Europe A/S, Marslev (DK)

( * ) Notice: Subject to any disclaimer, the term of this patent is extended or adjusted under 35 U.S.C. 154(b) by 127 days.

(21) Appl. No.: 13/385,117

(22) Filed: Feb. 2, 2012

(65) Prior Publication Data

US 2013/0205460 P1 Aug. 8, 2013

(51) Int. Cl.
*A01H 5/00* (2006.01)

(52) U.S. Cl.
USPC ..... Plt./360

(58) Field of Classification Search
USPC ..... Plt./360
See application file for complete search history.

*Primary Examiner* — June Hwu
(74) *Attorney, Agent, or Firm* — Barbara Campbell; Cochran Freund & Young, LLC

(57) ABSTRACT

A new *Osteospermum* plant particularly distinguished by having yellow flowers with dark greyed-purple disc florets and a compact and mounding plant habit.

1 Drawing Sheet

Genus and species: *Osteospermum hybrida.*
Variety denomination: 'SAKOST8194'.

BACKGROUND OF THE NEW PLANT

The present invention comprises a new and distinct variety of *Osteospermum*, botanically known as *Osteospermum hybrida*, and hereinafter referred to by the variety name 'SAKOST8194'. 'SAKOST8194' originated from a hybridization of the *Osteospermum* proprietary breeding line '205057' (unpatented) and the *Osteospermum* proprietary breeding line '205056' (unpatented) in Marslev, Denmark. The female parent, '205057' has a yellow flower color with an apricot center, and a compact and mounded plant habit. The male parent, '205057', has a yellow-orange flower color with a dark brown center and semi-erect plant habit.

In May 2006, the two *Osteospermum* lines '205057' and '205056' were crossed and seeds were obtained. The seeds were sown and approximately 100 plants were grown in pots for evaluation. Out of 100 $F_1$ lines, plant number 37 was selected which had a yellow flower color, dark disc florets, and compact and mounding plant habit.

In February 2007, plant number 37 was vegetatively propagated by cuttings and re-evaluated in an open field and a greenhouse. Plant number 37 was given the breeder code number '207307' and the stability of the distinct characteristics of this variety was confirmed.

In June 2007, plants from '207307' were evaluated again in pots and in an open field. '207307' was renamed 'SAKOST8194' and was found to reproduce true to type in successive generations of asexual propagation via vegetative cuttings.

SUMMARY

The following are the most outstanding and distinguishing characteristics of this new variety when grown under normal horticultural practices in Salinas, Calif.

1. Yellow flower color with dark greyed-purple disc florets; and
2. A compact and mounding plant habit.

DESCRIPTION OF THE PHOTOGRAPHS

This new *Osteospermum* plant is illustrated by the accompanying photographs which show the plant's overall plant habit including form, foliage, and flowers. The photographs are of a plant grown four months from transplant (five months from sticking) into 4-inch pots from rooted cuttings in Salinas, Calif. under greenhouse conditions in the spring of 2011. The colors shown are as true as can be reasonably obtained by conventional photographic procedures.

DESCRIPTION OF THE NEW VARIETY

Figure 1:
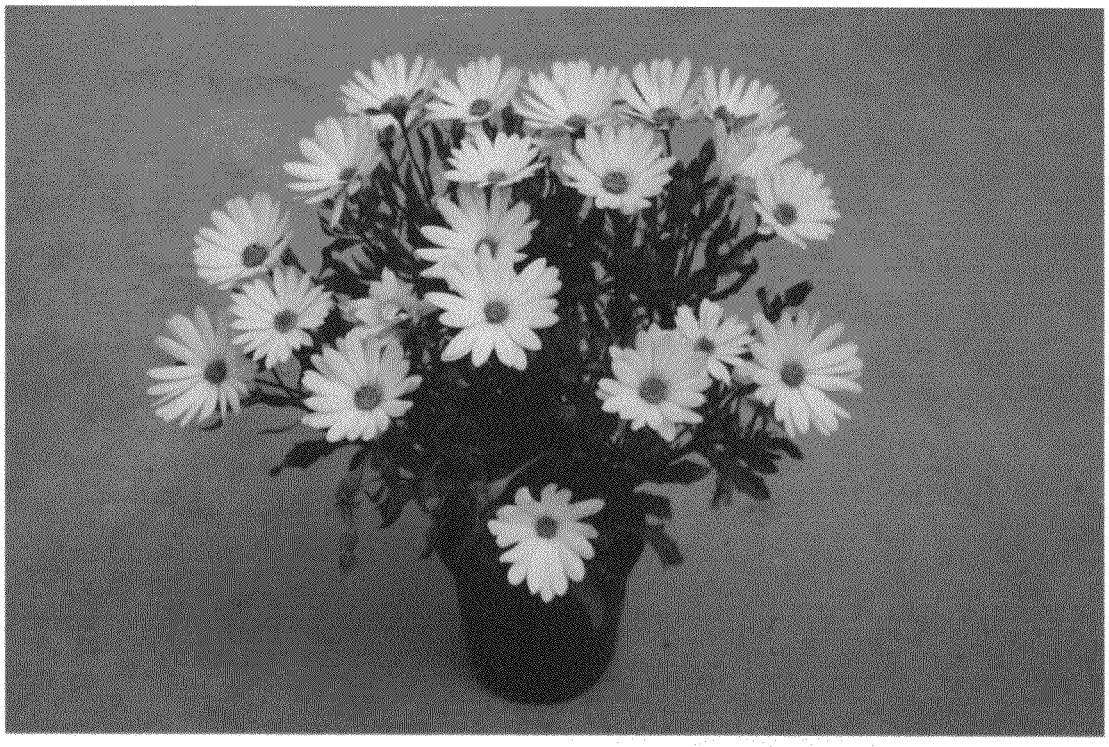
FIG. 1 shows the overall plant habit of the plant grown in a pot.
Figure 2:
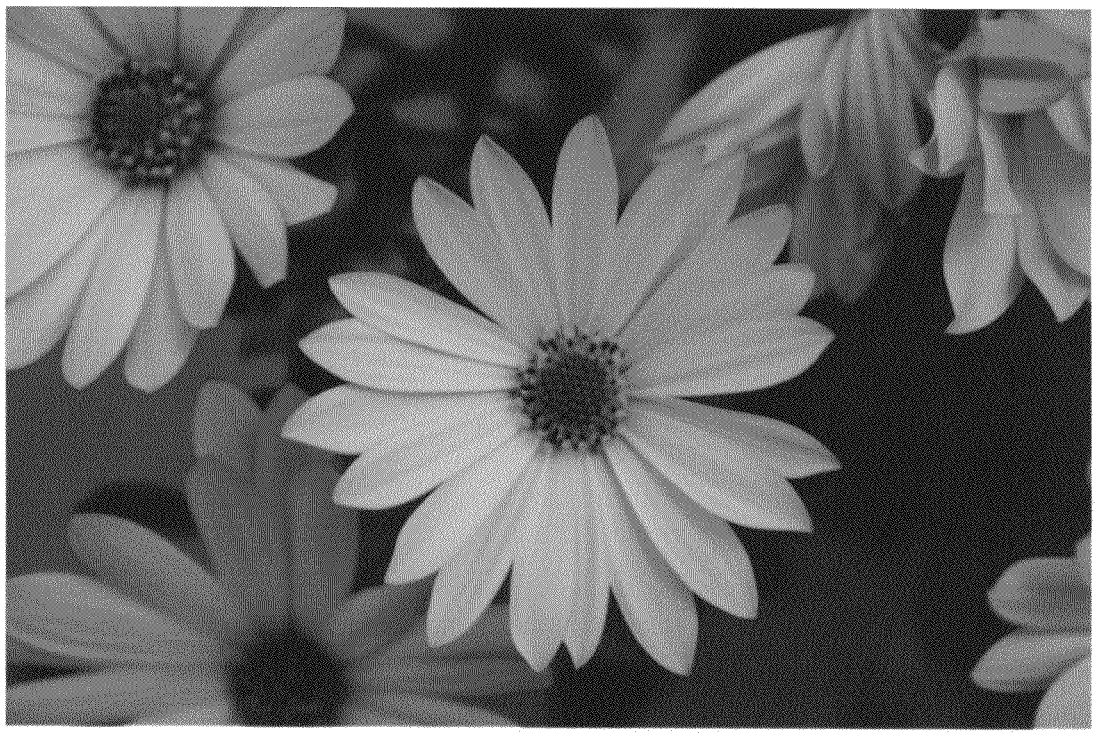
FIG. 2 shows a close-up of the mature inflorescence of the plant.

The following detailed descriptions set forth the distinctive characteristics of 'SAKOST8194'. The data which define these characteristics were collected from asexual reproductions via vegetative cuttings carried out in Salinas, Calif. Data was collected on plants grown approximately four months from transplant (five months from sticking) into 4-inch pots under greenhouse conditions in Salinas, Calif. in the winter of 2011. Color references are to The R.H.S. Colour Chart of The Royal Horticultural Society of London (R.H.S.), 4$^{th}$ edition.

Classification:

*Family.*—Compositae.
*Botanical.*—*Osteospermum hybrida.*
*Common.*—*Osteospermum*, Cape Daisy, South African Daisy.
*Designation.*—'SAKOST8194'.

Parentage:

*Female parent.*—The proprietary *Osteospermum* line '205057' (unpatented).

*Male parent.*—The proprietary *Osteospermum* line '205056' (unpatented).

Growth:

*Time to produce a rooted cutting.*—Cuttings will colonize a 2.5 cm diameter by 2.5 cm tall greenhouse tray cell with peat-based plant media in approximately four weeks. Cuttings are dipped in a normal dilution (1:9) of DIP 'N GROW, a liquid rooting concentrate root inducing solution in water. The trays are misted hourly during rooting.

*Environmental conditions for plant growth.*—Rooted cuttings are transplanted to pots with a 16 cm diameter, one plant per pot. Peat-based growing media is used. The pots are watered using a 150 ppm to 200 ppm fertilizer solution using 18-8-18 fertilizer. The soil is allowed to dry between watering. During the first few weeks after transplanting, the plants should have evening temperatures around 15° C. to 18° C. for good root growth. When plants reach 7.5 cm to 10 cm in height they are pinched back to 5 to 6 leaves to promote branching. Spring and summer daytime high temperatures in Salinas, Calif. where the data was collected, range from 16° C. to 25° C.

*Time to bloom from propagation.*—Approximately four weeks when rooted vegetative cuttings are transferred to a 4 inch diameter pot. Flowering season is all year in the United States when grown in a greenhouse, when grown outdoors, it is spring to fall. Vernalization is not required to induce flowering.

Plant description:

*Habit.*—Compact and mounding.
*Life cycle.*—Annual.
*Form.*—Compact and mounding.
*Height (from soil line to first node).*—0.5 cm.
*Height (from soil line to top of foliage).*—36.0 cm to 38.0 cm.
*Width.*—58.0 cm to 60.0 cm.

Stems:

*General.*—Multiple; circular in cross-section.
*Stem length (total).*—14.0 cm to 15.0 cm.
*Diameter.*—0.2 cm.
*Internode length.*—4.0 cm.
*Color.*—RHS 144A (Yellow-green) with RHS 187A (Greyed-purple) anthocyanin.
*Pubescence.*—Moderate. Color: RHS N155A (White). Shape: Short, hair-like, fibers.
*Anthocyanin color.*—Slight, RHS 187A (Greyed-purple).

Branches:

*General.*—Circular in cross-section.
*Number of main branches.*—1.
*Total number of branches.*—8.
*Length.*—11.0 cm to 12.0 cm; approximately 1.0 cm from soil line to first node, 2.0 cm between first and second nodes.
*Diameter.*—0.3 cm.
*Internode length.*—2.0 cm.
*Color.*—RHS 144A (Yellow-green) with RHS 187A (Greyed-purple) anthocyanin.
*Pubescence.*—Very slight.
*Pubescence shape.*—Short, hair-like fibers.
*Pubescence color.*—RHS N155A (White).
*Anthocyanin color.*—RHS 187A (Greyed-purple).

Leaves:

*Arrangement.*—Alternate.
*Shape.*—Oblanceolate.
*Apex.*—Acute.
*Base.*—Attenuate.
*Margin.*—Serrate.
*Venation.*—Pinnate.
*Surface (both surfaces).*—Dull.
*Surface pubescence (both surfaces).*—Slight, mainly around edge.
*Surface pubescence color.*—RHS N155A (White).
*Attachment.*—Decurrant.
*Length.*—5.5 cm.
*Width.*—1.5 cm.
*Thickness.*—Less than 0.1 cm.
*Color.*—Upper surface: RHS 143A (Green). Lower surface: RHS 143B (Green).
*Venation color.*—Upper surface: RHS 144B (Yellow-green). Lower surface: RHS 144C (Yellow-green).

Inflorescence:

*Number per plant.*—24.
*Type.*—Capitulum (head); disc florets are perfect and ray florets are carpellate.
*Flowering habit.*—Determinate.
*Lastingness of inflorescence on the plant.*—3 to 4 days.
*Fragrance.*—Absent.
*Seed production.*—None observed.
*Diameter.*—7.0 cm to 8.0 cm.
*Depth.*—2.0 cm.
*Ray floret number.*—18 to 24 per inflorescence.
*Disc diameter.*—1.2 cm.
*Disc floret number.*—60 to 80 per inflorescence.
*Peduncle length.*—5.0 cm from inflorescence to first node.
*Peduncle diameter.*—0.2 cm.
*Peduncle color.*—RHS 144A (Yellow-green) with RHS 187A (Greyed-purple) anthocyanin.
*Peduncle texture.*—Dull, slight pubescence.
*Phyllaries.*—Arrangement: 21 per inflorescence, free, arranged symmetrically. Length: 1.2 cm. Width: 0.7 cm. Apex: Acute. Margin: Entire. Shape: Linear; acute. Color (for both upper and lower surfaces): RHS 143A (Green).

Ray florets (ligules):

*Corolla.*—One ray per ray floret; only the outer row of florets are the ray florets.
*Number of ray florets.*—18 to 24 per inflorescence.
*Length.*—3.2 cm.
*Width.*—0.7 cm.
*Shape.*—Lanceolate.
*Apex.*—Acute.
*Margin.*—Entire.
*Base.*—Fused.
*Color.*—Upper surface: RHS 6A (Yellow). Lower surface: RHS 6A (Yellow) with RHS N186C (Greyed-purple) stripes or streaks.
*Pubescence.*—Glabrous.

Disc florets:

*Color.*—Darker than RHS N187A (Greyed-purple).
*Shape.*—Tubular.
*Apex.*—Pointed.
*Texture.*—Dull, pubescent.
*Size.*—Length: 0.6 cm. Width: 0.1 cm.

Reproductive organs:

*Ovary.*—Superior.
*Pistil form.*—One style with two stigma branches.
*Pistil length.*—0.5 cm.
*Stigma color.*—RHS 187A (Greyed-purple).

*Style color.*—RHS 155A (White).
*Stamens.*—5, fused into a single tube.
*Anther color.*—RHS 187A (Greyed-purple).
*Pollen color.*—RHS 17A (Yellow-orange).
*Filament color.*—RHS 155A (White).

Disease and insect resistance: No known resistance or susceptibility.

COMPARISON WITH PARENTAL LINES AND KNOWN VARIETY

'SAKOST8194' is a distinct variety of *Osteospermum* having yellow colored flowers with dark disc florets, and a compact and mounding plant habit. 'SAKOST8194' is distinguished from its parents as described in Table 1 (color references are to The Royal Horticultural Society Colour Chart, 4$^{th}$ edition).

TABLE 1

Comparison with Parental Lines

| Characteristic | 'SAKOST8194' | Male Parent '205056' | Female Parent '205057' |
|---|---|---|---|
| Ray floret (ligule) color, upper surface | RHS 6A (Yellow) | Yellow-orange | Yellow |
| Plant growth habit | Compact and mounding | Semi-erect | Compact and mounding |
| Flower center color | Darker than RHS N187A (Greyed-purple) | Dark brown | Apricot |

'SAKOST8194' is a distinct variety of *Osteospermum* having yellow colored flowers with dark disc florets, and a compact and mounding plant habit. 'SAKOST8194' is most similar to the *Osteospermum* plant named 'Saksisgolye' (U.S. Plant Pat. No. 19,602). Differences between the two varieties are described in Table 2 (color references are to The Royal Horticultural Society Colour Chart, 4$^{th}$ edition).

TABLE 2

Comparison with Similar Variety

| Characteristic | 'SAKOST8194' | 'Saksisgolye' |
|---|---|---|
| Ray floret (ligule) color, upper surface: | RHS 6A (Yellow) | RHS 12C (Yellow) with slight streaking of RHS 187C (Greyed-purple) and RHS 187C (Greyed-purple) at the tip |
| Ray floret (ligule) color, lower surface: | RHS 6A (Yellow) with RHS N186C (Greyed-Purple) stripes or streaks | RHS 187C (Greyed-Purple) with RHS 12B (Yellow) streaks and RHS 187A (Greyed-Purple) at the tip |
| Plant habit | Compact and mounded | Very compact and branching |

I claim:

1. A new and distinct variety of *Osteospermum* plant as shown and described herein.

* * * * *